United States Patent [19]

Johnson

[11] Patent Number: 5,460,625
[45] Date of Patent: Oct. 24, 1995

[54] CRYOGENIC RESISTANT COEXTRUDED TUBING

[75] Inventor: Kenneth M. Johnson, Lindenhurst, Ill.

[73] Assignee: Baxter International Inc., Deerfield, Ill.

[21] Appl. No.: 560,698

[22] Filed: Jul. 31, 1990

[51] Int. Cl.$^6$ .................................................. A61M 5/00
[52] U.S. Cl. ........................ 604/403; 604/408; 604/415
[58] Field of Search ......................... 604/403, 408–415; 428/515–520, 376; 215/DIG. 3

[56] References Cited

U.S. PATENT DOCUMENTS

| | | |
|---|---|---|
| 3,561,493 | 2/1971 | Maillard et al. . |
| 3,931,449 | 1/1976 | Hirata et al. . |
| 4,123,576 | 10/1978 | Kobayashi et al. . |
| 4,131,200 | 12/1978 | Rinfrat .................... 604/410 X |
| 4,222,379 | 9/1980 | Smith . |
| 4,223,675 | 9/1980 | Williams . |
| 4,327,726 | 5/1982 | Rwong et al. ............ 604/408 X |
| 4,329,992 | 5/1982 | Becker et al. ............ 604/403 |
| 4,332,122 | 6/1982 | Williams . |
| 4,376,799 | 3/1983 | Tusim ......................... 604/339 |
| 4,465,487 | 8/1984 | Nakamura et al. . |
| 4,479,989 | 10/1984 | Mahal ....................... 604/408 X |
| 4,482,585 | 11/1984 | Ohodaira et al. ........... 604/408 X |
| 4,505,708 | 3/1985 | Gajewski et al. ............ 604/400 |
| 4,516,977 | 5/1985 | Herbert . |
| 4,540,416 | 9/1985 | Hattori et al. . |
| 4,543,281 | 9/1985 | Pedersen et al. . |
| 4,553,970 | 11/1985 | Lewis, Jr. . |
| 4,557,959 | 12/1985 | Kuehlein et al. . |
| 4,561,110 | 12/1985 | Herbert ....................... 604/408 |
| 4,573,980 | 3/1986 | Karrasch et al. . |
| 4,612,340 | 9/1986 | Ohachi . |
| 4,636,412 | 1/1987 | Field . |
| 4,657,542 | 4/1987 | Ohachi ....................... 604/410 |
| 4,687,711 | 8/1987 | Vietto et al. .............. 604/374 X |
| 4,700,838 | 10/1987 | Falciani et al. . |
| 4,810,542 | 3/1989 | Kawai et al. . |
| 4,837,047 | 6/1989 | Sato et al. . |

*Primary Examiner*—Sam Rimell
*Attorney, Agent, or Firm*—Robert M. Barrett; Bradford R. L. Price; Joseph B. Barrett

[57] ABSTRACT

The present invention provides a coextruded tubing that has been optimized for usage in cryogenic freezing applications. To this end, a coextruded tubing is provided having three layers, a first layer of ethylene vinyl acetate; a second layer of polyolefin; and a third layer of polyvinyl chloride. An improved container for use in cryogenic freezing applications is also provided.

16 Claims, 1 Drawing Sheet

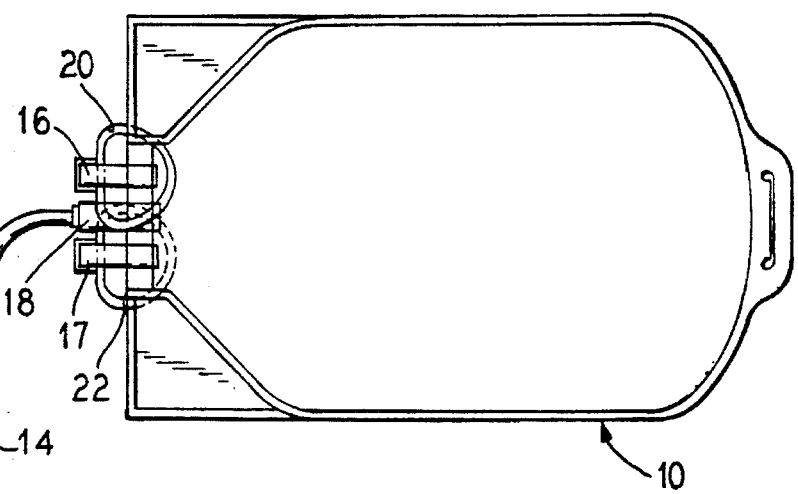
FIG. 1
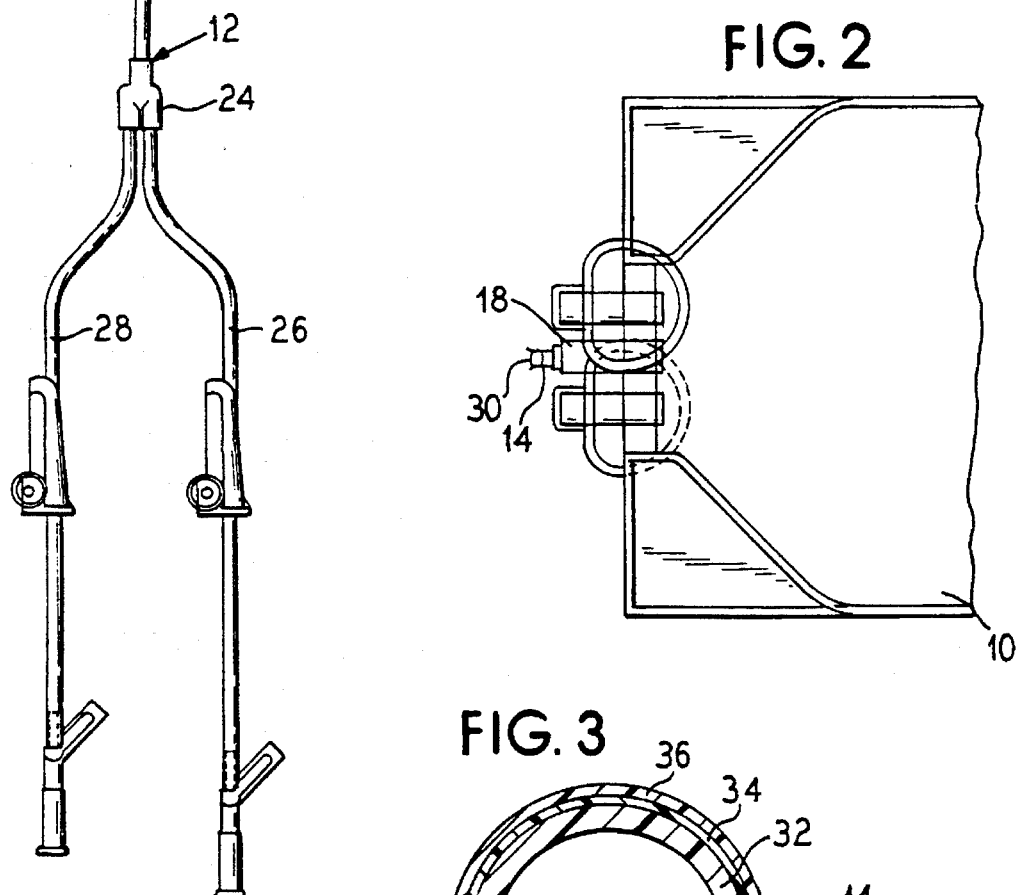
FIG. 2
FIG. 3
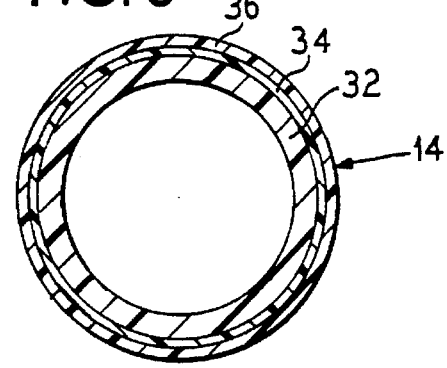

CRYOGENIC RESISTANT COEXTRUDED TUBING

BACKGROUND OF THE INVENTION

The present invention relates generally to tubings for accessing a container. More specifically, the present invention relates to a tubing for a container having cryogenic freezing applications.

Tubings are utilized with containers to access the interior of the container. The tubing provides a fluid path from the container to a second environment. This fluid path is utilized to place material within the container or access material contained therein.

It is known to house within a container biological fluids including cellular material and blood components. These fluids are typically added to the containers by use of a tubing that is connected to a port that extends from the container. The components are fed from a supply source into the container through the tubing. After the components are fed to the container, and if desired samples are taken therefrom, the tubing is sealed and cut. Typically, the tubing is cut and sealed as close to the port as possible providing a tubing remnant.

In order to store the fluids housed within the container, the container and material may be frozen by being subjected to very low temperatures, for example, frozen in a liquid nitrogen environment (−196° C.). When exposed to a liquid nitrogen environment, the flexible containers are thermally stressed. When so stressed, the containers are at risk of breaking or other failure.

Some prior flexible containers for uses that include the storage of cellular matter and blood components that are frozen in a liquid nitrogen environment, utilize a polyvinyl chloride extruded tubing formulation. When frozen in liquid nitrogen, the polyvinyl chloride tubing remnants become extremely brittle. Indeed, the frozen tubing will not tolerate any significant flexure or impact without fracture. In order to utilize these containers, it is typically necessary to employ, when the containers are frozen, a protective canister (thin, rectangular aluminum plate cassette) to obviate any stress than can induce failure of the tubing.

Although the use of a protective canister reduces the risk of failure of the tubing, there are still circumstances in which there are product failures. For example, containers that house larger fluid volumes are commonly tethered by a cord and suspended in a liquid phase of cryogenic solutions wherein the tubing remnant cannot be adequately protected.

SUMMARY OF THE INVENTION

The present invention provides a coextruded tubing that has been optimized for use in cryogenic freezing applications. To this end, a coextruded tubing is provided having three layers: a first layer of ethylene vinyl acetate; a second layer of polyolefin; and a third layer of polyvinyl chloride.

In an embodiment, the polyolefin is an acrylic acid based polymer.

In an embodiment of the coextruded tube of the present invention, the first layer has a thickness of approximately 0.003 to about 0.013 inches, the second layer has a thickness of approximately 0.004 inches, and the third layer has a thickness of approximately 0.003 to about 0.013 inches.

An improved container for use in cryogenic freezing applications is also provided including a tubing for filling the container that is secured to a port of the container. The container is constructed from ethylene vinyl acetate and the tubing is constructed from a coextruded material including an inner layer of ethylene vinyl acetate, an outer layer of polyvinyl chloride, and a middle layer of a polyolefin adhesive material.

In an embodiment, the port of the container is constructed from a coextruded material and has an outer layer of ethylene vinyl acetate and an inner layer of polyvinyl chloride.

Additional features and advantages of the present invention are described in, and will be apparent from, the detailed description of the presently preferred embodiments and from the drawings.

BRIEF DESCRIPTION OF THE DRAWINGS

FIG. 1 illustrates a perspective view of a container with attached set including the coextruded tubing of the present invention.

FIG. 2 illustrates a portion of the container of FIG. 1 including a coextruded tubing remnant.

FIG. 3 illustrates a cross-sectional view of an embodiment of the coextruded tubing of the present invention.

DETAILED DESCRIPTION OF THE PRESENTLY PREFERRED EMBODIMENTS

The present invention provides an improved tubing for accessing a flexible container. More specifically, the present invention provides a coextruded tubing for use with a container in cryogenic freezing applications.

Referring to FIG. 1, a container 10 including a set 12 having an embodiment of the coextruded tubing 14 of the present invention is illustrated. Of course, although the coextruded tubing of the present invention is illustrated with a specific set and container, it should be appreciated that the coextruded tubing can be used with other sets and containers.

In the embodiment of the invention illustrated in FIG. 1, the container 10 is provided with the set 12, that includes the tubing 14, so as to allow the container to be filled with a biological fluid, for example, a blood component or cellular material. This blood component or cellular material can then be frozen for storage in the container 10 at a very low temperature, e.g., liquid nitrogen temperature. The container 10 provides means for housing the material, both in a frozen and non-frozen state. In a preferred embodiment, the container 10 is constructed from ethylene vinyl acetate.

As illustrated, the container 10 includes, in the embodiment illustrated, three ports or tubes 16, 17, and 18, respectively. Two of the ports 16 and 17 include "D" ring closures 20 and 22, respectively, that provide a sterile barrier for the ports 16 and 17. These ports 16 and 17 are used to access the material contained within the container 10 through the use of a spike or other means. The ports 16 and 17 include membranes (not illustrated) that are pierced, after the "D" ring closures 20 and 22 are removed, by a spike to access the material contained within the container 10.

The middle port 18 is used, in the illustrated embodiment, to fill the container 10. To this end, secured within the middle port 18 is a set 12 including the tubing 14 of the present invention. To secure the set 12 to the container, the tubing 14 of the present invention, is inserted within the port 18 and sealed therein. When so sealed, an interior of the tubing 14 is in fluid communication with an interior of the container 10 allowing the tubing to be utilized to fill the container. In a preferred embodiment, the ports 16, 17, and 18 are constructed from a coextruded material having an outer layer of ethylene vinyl acetate, an inner layer of polyvinyl chloride, and a tie layer.

In the illustrated embodiment, the set 12 includes a Y-connector 24 that connects the tubing 14 of the present invention to additional tubings 26 and 28 which can be utilized to fill the container 10. The set 12 in addition to being utilized to fill the container 10 can also be utilized to sample the contents of the container 10 prior to sealing off the tubing 14 and thereby the container. Although, in the illustrated embodiment, the set 12 includes a Y-connector 24 and two tubings 26 and 28, additional fluid paths can be utilized. Likewise, if desired, only one fluid path can be utilized. Multiple fluid tubings provide multiple access if desired. For example, one tubing can be used to place cells within the container and the other tubing can be used to infuse cell media or a cryoprotector, such as DMSO.

Referring now to FIG. 2, once the container 10 has been filled with the desired contents, and the contents have been sampled for a final time, the tubing 14 is sealed and cut to provide a sealed container. Typically, the tubing 14, as illustrated in FIG. 2, is sealed and cut so that only a small portion of the tubing 14 remains as a remnant 30. The sealing and cutting of the tube 14 can be accomplished, for example, by dielectric sealing. The remnant 30 functions to seal the port 18 of the container 10 and therefore, the maintenance of the remnant's integrity is critical. To maintain the integrity of the remnant 30 at low temperatures, the tubing 14 is constructed from the composition of the present invention.

Referring now to FIG. 3, a cross-sectional perspective view of the coextruded tubing 14 of the present invention is illustrated. The tubing 14 is produced through a coextrusion process that provides for three distinctively different materials to be simultaneously, concentrically layered down adjacent to one another. The coextruded tubing 14 of the present invention provides a tubing that has specifically desirable characteristics for use in cryogenic applications.

As illustrated, the coextruded tubing 14 comprises three layers: a first layer 32 of ethylene vinyl acetate; a second layer 34 of polyolefin; and a third layer 36 of polyvinyl chloride. Preferably, the polyolefin is a an acrylic acid based polymer. It has been found that polyolefins available from DuPont under the designations Bynel CXA 1123 and 1124 function satisfactorily.

The inner layer 32 of the tube 14 is formed of ethylene vinyl acetate that provides physical properties that function to enhance flexural, tensile, and/or impact failure resistance while in a frozen crystalline state. The polyolefin, middle layer 34, functions to knit the inner and outer material layers to one another. The middle layer 34 reduces any tendencies of the inner and outer layers 32 and 36, respectively, to delaminate. The outer layer 36 of polyvinyl chloride provides a gamma sterilizable substrate. The outer layer 36, in a preferred embodiment, is solvent (cyclohexanone) bonded to the port 18 of the container 10.

By way of example, and not limitation, examples of the coextruded tubing structure 14 of the present invention will now be given.

Five different layer thicknesses were extruded. The tubes were coextruded to have an inner diameter of approximately 0.118 inches and an outer diameter of approximately 0.158 inches. This dimension provides a thickness that affords the tube dielectric sealability. The five test geometries were as follows:

| DESIGNATION | (OUTER) PVC | (CENTER) ACRYLIC ACID BASED POLYMER | (INNER) EVA |
|---|---|---|---|
| A | .003 | .004 | .013 |
| B | .005 | .004 | .011 |
| C | .008 | .004 | .008 |
| D | .013 | .004 | .003 |
| E | .011 | .004 | .005 |

(All dimensions are in inches.)

The tubings were tested by being filled with water and were pre-frozen in an −80° C. freezer. The pre-freezing minimizes the reaction when dipped in liquid nitrogen. When each type of the tubing was removed from the liquid nitrogen, it was immediately dropped from approximately 7 feet. Additionally, the tubings were subjected to a bending motion in an attempt to break the tubing. This is an indicator of how the tubing will resist fracture in actual use. These tubings were also tested against a standard PVC tube.

The results of the tests were as follows:

| Tubing Type | Drop Test | Bend Test |
|---|---|---|
| PVC (Prior Art) | Shattered on Impact | Immediate Fracture |
| E | Few Breaks | Breakable With Minor Effort |
| D | Few Breaks | Breakable With Increased Effort |
| C | No Breaks | Will Break With Significant Effort |
| B | No Breaks | Tubing Wanted to Bend Rather Than Break or Fracture |
| A | No Breaks | Tubing Wanted to Bend Rather Than Break or Fracture |

The above tests, in addition to testing relating to tensile strength, heat sealability, and solvent bondability, demonstrate that the coextruded tubing of the present invention is better suited for cryogenic container tubing applications than the prior art PVC tubes. The tubing of the present invention provides the following properties.

No tensile induced delamination

Dielectrically sealable/separable

Very resistant to shock and bending

Adequate tensile strength prior to ultimate failure

Adequate solvent bond strength

An example of the tubing of the present invention that applicant believes will function satisfactorily is as follows.

The overall tube has an inner diameter of approximately 0.115 to about 0.121 inches and an outer diameter of approximately 0.157 to about 0.163 inches. The tube is constructed from a coextruded material having the following layers: an inner layer of ethylene vinyl acetate having a thickness of approximately 0.003 to about 0.013 inches; an outer layer of polyvinyl chloride having a thickness of 0.003 inches to about 0.013 inches of the total thickness of the tubing; and a middle layer of an acrylic acid based polymer having a thickness of approximately 0.004 inches.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

I claim:

1. A coextruded tube for a container comprising:

a first layer of ethylene vinyl acetate;

a second layer of polyolefin; and a third layer of polyvinyl chloride, the tube providing cryogenic properties.

2. The coextruded tube of claim 1 wherein the layer of polyvinyl chloride is bonded to a portion of the container.

3. The coextruded tube of claim 1 wherein the polyolefin is an acrylic acid based polymer.

4. The coextruded tube of claim 1 wherein:

the first layer has a thickness of approximately 0.003 to about 0.013 inches;

the second layer has a thickness of approximately 0.004 inches; and the third layer has a thickness of approximately 0.003 to about 0.013 inches.

5. The coextruded tube of claim 2 wherein the portion of the container is a port extending from the container.

6. A container including a body and a coextruded tube extending from the body, the tube comprising:

an inner layer of ethylene vinyl acetate;

an outer layer of polyvinyl chloride; and a middle layer of polyolefin, the tube providing cryogenic properties.

7. The container of claim 6 wherein the layer of polyvinyl chloride is bonded to a port extending from the container.

8. The container of claim 6 wherein the port is constructed from a coextruded material and has an outer layer of ethylene vinyl acetate and an inner layer of polyvinyl chloride.

9. The container of claim 6 wherein with respect to the tubing:

the first layer has a thickness of approximately 0.003 to about 0.013 inches;

the second layer has a thickness of approximately 0.004 inches; and the third layer has a thickness of approximately 0.003 to about 0.013 inches.

10. The container of claim 6 wherein the polyolefin is an acrylic acid based polymer.

11. The container of claim 6 wherein the body of the container is constructed from ethylene vinyl acetate.

12. A plastic container for use in cryogenic freezing applications including a tubing for filling the container secured to a port of the container wherein:

the container is constructed from ethylene vinyl acetate; and the tubing is constructed from a coextruded material and includes:

an inner layer of ethylene vinyl acetate;

an outer layer of polyvinyl chloride; and a middle layer of a polyolefin adhesive material, the tube providing cryogenic properties.

13. The container of claim 12 wherein the port is constructed from a coextruded material and has an outer layer of ethylene vinyl acetate, an inner layer of polyvinyl chloride, and a tie layer.

14. The container of claim 12 wherein with respect to the tubing:

the first layer has a thickness of approximately 0.003 to about 0.013 inches;

the second layer has a thickness of approximately 0.004 inches; and the third layer has a thickness of approximately 0.003 to about 0.013 inches.

15. The container of claim 12 wherein the polyolefin is an acrylic acid based polymer.

16. The container of claim 12 wherein the tubing has an inner diameter of approximately 0.115 to about 0.121 inches and an outer diameter of approximately 0.157 to about 0.163 inches.

* * * * *